United States Patent

[19]

Petersen

[11] 4,039,587
[45] Aug. 2, 1977

[54] METHOD OF PREPARING POLYNUCLEAR, HALOGENATED, AROMATIC BENZYL ETHERS

[75] Inventor: Egon Norbert Petersen, Neunkirchen-Seelscheid, Germany

[73] Assignee: Dynamit Nobel Aktiengesellschaft, Troisdorf, Germany

[21] Appl. No.: 610,478

[22] Filed: Sept. 4, 1975

Related U.S. Application Data

[62] Division of Ser. No. 541,669, Jan. 16, 1975, abandoned.

[30] Foreign Application Priority Data

Feb. 2, 1974 Germany .............................. 2404999

[51] Int. Cl.$^2$ .............................................. C07C 41/04
[52] U.S. Cl. ........................... 260/612 R; 260/613 R; 8/116 R; 252/8.9
[58] Field of Search .................... 260/612 R, 613 R

[56] References Cited

U.S. PATENT DOCUMENTS

| 2,109,514 | 3/1938 | Van Duzee et al. | 260/612 R |
| 2,121,723 | 6/1938 | Bass et al. | 260/612 R |
| 2,121,724 | 6/1938 | Bass et al. | 260/612 R |
| 3,450,772 | 6/1969 | Bridger et al. | 260/613 R |
| 3,654,364 | 4/1972 | Meckel et al. | 260/613 R X |

OTHER PUBLICATIONS

Powanol — Glycol Ether Solvents (1957), p. 3.

*Primary Examiner*—Bernard Helfin
*Attorney, Agent, or Firm*—Burgess, Dinklage & Sprung

[57] ABSTRACT

An aromatic polynuclear, halogenated, aromatic benzyl ether of the formula

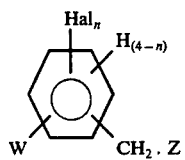

I wherein W is a chlorine or bromine atom or a methyl radical or the radical —CH$_2$.Z, said radical W being disposed in the ortho, meta or para position with respect to the CH$_2$.Z radical, Hal represents a chlorine or bromine atom, $n$ is 0 to 4 and Z represents a phenoxy radical of the general formula

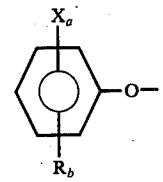

II wherein X is a chlorine or bromine atom, R is a hydrogen atom or an alkyl radical having 1 to 4 carbon atoms, $a$ is 2 to 5 and $b$ is (5-$i$ $a$); a process for producing such polynuclear halogenated benzyl ether by contacting a benzyl halide of the general formula

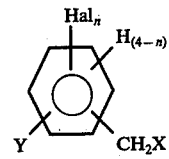

III wherein Hal and $n$ have the previously assigned significance, X is a chlorine or bromine atom, Y is the same as CH$_2$X or is a hydrogen or chlorine atom or a methyl radical and is disposed in the ortho, meta or para position with respect to the radical —CH$_2$X, and a phenolate of a halogen phenol which halogen phenol has the formula

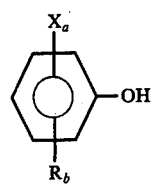

IV wherein X, R, $a$ and $b$ have the previously assigned significance, in a glycol monoalkyl ether reaction medium until the ether is formed and thereafter isolating the ether.

12 Claims, No Drawings

METHOD OF PREPARING POLYNUCLEAR, HALOGENATED, AROMATIC BENZYL ETHERS

BACKGROUND OF THE INVENTION

1. Field of the Invention

This is a div. of appl. S.N. 541,669, filed Jan. 16, 1975 and now abandoned. This invention is directed to polynuclear, halogenated, aromatic benzyl ethers. This invention is also directed to a process for the preparation of the same from benzyl halides and phenolates, particularly benzyl halides having chloro or bromo nuclear substitution and phenolates having chloro and bromo substitution of the phenol ring. This invention is also directed to the use of such aromatic, polynuclear, halogenated benzyl ethers in the treatment of fibers and fabrics to render them water repellent.

SUMMARY OF THE INVENTION

Broadly, this invention contemplates an aromatic, polynuclear, halogenated benzyl ether having the formula:

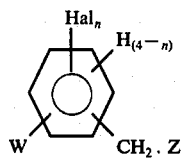

I wherein W is a chlorine or bromine atom, a methyl radical, or the radical —$CH_2$. Z, said moiety W being disposed in the ortho, meta or para position with respect to the $CH_2$. Z moiety; Hal is chlorine or bromine, $n$ is 0 to 4 and Z is a phenoxy radical of the formula:

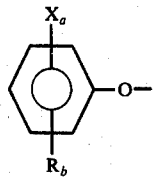

II wherein X is chlorine or bromine, R is a hydrogen atom, an alkyl radical having 1 to 4 carbon atoms, $a$ is 2 to 5 and $b$ is $(5-a)$. Specifically contemplated aromatic polynuclear, halogenated benzyl ethers are those prepared by a process which comprises contacting a benzyl halide of the formula:

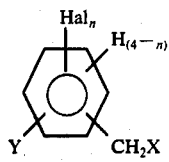

III wherein Hal and $n$ have the previously assigned significance, X is a chlorine or bromine atom, Y is the same as $CH_2X$ or is a hydrogen or chlorine atom or a methyl radical and said moiety Y is disposed in the ortho, meta or para position with respect to the radical —$CH_2X$ with a phenolate of a halogen phenol which halogen phenol has the formula:

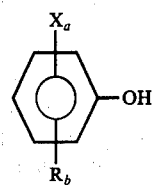

IV wherein X, R, $a$ and $b$ have the previously assigned significance in a glycol monoalkyl ether reaction medium.

According to the invention it has been discovered that numerous aromatic polynuclear, halogenated benzyl ethers having the formula expressed above can be prepared. These can be prepared employing equally molecular amounts of the benzyl halide and phenolate. There can be prepared simple ethers such as 4-methyl-2,3,5,6-tetrachlorobenzyl alcohol-(1)-(pentachlorophenyl)-ether as well as ethers which contain two moieties derived from the phenoxy group, e.g., 2,3,5,6-tetrachloro-1,4-xylylene-glycol-bis-(pentachlorophenyl)-ether and its isomers.

It has been found that numerous starting benzyl halides having formula III can be employed in the process of the invention. These include in particular pentachlorobenzylchloride 1-methyl-2-chloromethyl-3,4,5,6-tetrachlorobenzene, 1-methyl-3-chloromethyl-2,4,5,6-tetrachlorobenzene, 1-methyl-4-chloromethyl-2,3,5,6-tetrachlorobenzene, the isomeric o-, m- and p-methylbromomethyltetrachlorobenzenes, 1,2-bis-(chloromethyl)-3,4,5,6-tetrachlorobenzene, and bromomethyl compounds corresponding to the foregoing, 3-bis-(chloromethyl)-2,4,5,6,-tetrachlorobenzene, 1,3-bis-(bromomethyl)-2,4,5,6-tetrachlorobenzene, 1,4-bis-(chloro- or bromomethyl)-2,3,5,6-tetrachlorobenzene, α,α'-dichloro(bromo)-p-xylene and others.

Accordingly, the starting benzyl halide can be either monofunctional or bifunctional benzyl halides, the bifunctional benzyl halides being those which have the substitutents -$CH_2Cl$ or —$CH_2Br$ in the ortho, meta or para position with respect to one another and whose other positions, as represented in formula III, are occupied by chlorine and/or bromine atoms and/or hydrogen atoms. For example, from 1,4-bis-(chloromethyl)-2,3,5,6-tetrachlorobenzene and pentabromophenol sodium one obtains the ether having the formula:

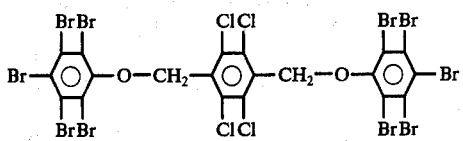

V

The above-named benzyl halides are easily produced technically through a halogenation of the corresponding aromatics, such as for example the isometric xylenes or toluene. Such a process is described in German "Auslegeschrift" 1,568,607, and also in Belgian Pat. 631,170. The preparation of pentachlorobenzyl chloride is described in U.S. Pat. Nos. 2,698,592. The bromomethyl compounds can be prepared easily from the chloromethyl compounds in accordance with a hitherto unpublished patent application Ser. No. 445,133 assigned to the assignee hereof and hereby incorporated herein by reference.

In phenolates, the alkali salts are used preferentially, especially the sodium or potassium salts of halogen phenols. The following are examples of halogen phenols of general formula IV: pentachlorophenol, 2,4-dichloro-6-methylphenol, 2,5-dichloro-6-methylphenol, 2,4,6-trichlorophenol, 2,4,6-tribromophenol, 2,3,4,6-tetrachlorophenol, pentabromophenol, 2,4,6-trichloro-3,5-dimethylphenol, 2,4-dichloro-3-methyl-6-tert.-butylphenol, and 4,5-dichloro-2,6-di-tert.-butylphenol.

Where $R_b$ is alkyl, and $b$ is 2 or 3 the alkyl groups can be the same as one another or different. Where R is alkyl those phenols are preferred in accordance with the invention in which R in formula IV represents methyl and $b$ represents 1 or 2, and, if $b$ is 2, the methyl groups are in the meta or para position with respect to one another. Fundamentally, alkaline earth salts can also be used instead of the alkali salts.

In the practice of the process of the invention, it is unnecessary to charge the reactor with a pre-prepared phenolate. Indeed, it is especially advantageous to produce the phenolate in situ wherein, for example, a source of the phenol and a source of the alkali or alkaline earth metal, e.g., alkali or alkaline earth metal hydroxides are charged into the reactor. Thereafter, there can be added to the same reactor benzyl halide and the reaction can take place without separation of any water which might be present in the alkali or alkaline earth metal hydroxide solution so introduced.

The preparation of the new aromatic halogenated polynuclear benzyl ethers of general formula I is performed in accordance with the invention at elevated temperature in a solvent suitable for the phenolates.

It has been found that the reaction takes place particularly smoothly and results in high yields and high volume-time yields if glycol monoalkyl ethers are used. Largely pure ethers are principally obtained, which can be used for most purposes without further refinement. The yields are as a rule at least 80% by weight and more. Such a successful outcome was not foreseeable, since secondary reactions of the solvent were to be expected. Glycol monoalkyl ethers have proven desirable for the performance of the method of the invention also because the phenolates used in accordance with the invention are easily dissolved by them in sufficient quantity.

Moreover, the half-ethers of glycols have the additional advantage of boiling points above 100° C, which has a very advantageous effect on the reaction times and yields. This makes it possible to operate at normal pressure, which is not the case when low-boiling solvents are used, since a smooth and rapid reaction is assured only at temperatures above 60° C. If, for example, the reaction is performed in tetrahydrofuran, at the reflux temperature of tetrahydrofuran, which is also a good solvent for pentachlorophenol sodium for example, the desired products are obtained only in a very poor yield. Furthermore, the glycol ethers are inexpensive and therefore economical solvents.

The following glycol monoalkyl ethers, for example, can be used as solvents and reaction media in the practice of the method of the present invention: 1,4-butanediol monomethyl ether, 1,4-butanediol monoethyl ether, 2,3-butyleneglycol monoethyl ether, propylene glycol monomethyl ether, propylene glycol monoethyl ether, ethylene glycol monobutyl ether, ethylene glycol monoethyl ether, ethylene glycol monomethyl ether, or mixtures of same. The last two, i.e., methyl glycol or ethyl glycol, are preferably used for the process of the invention. Generally, the monoalkyl ethers which can be employed according to the invention have between 1 and 4 carbon atoms in the alkyl group and a main chain length between 2 and 4 carbon atoms. Generally, the basic alcohol had between 2 or 3 hydroxyl groups.

DESCRIPTION OF PREFERRED EMBODIMENTS

In the practice of the present invention it is particularly desirable to introduce the monoalkyl glycol into the reaction vessel, thereafter introduce the alkali or alkaline earth metal hydroxide to the monoglycol ether, preferably employing a sodium or potassium hydroxide. The metal hydroxide can be added in substance, but is preferably added in the form of a 40 to 50% aqueous solution. A clear, complete mixture is rapidly and readily obtained into which the halophenol is then stirred in an equimolecular quantity, for example. Of course, the phenol can also be dissolved beforehand, it being desirable to use the reaction mixture as the solvent, such as methyl or ethyl glycol for example.

The ratio of the glycol monoether to the phenolate is best made such that a homogeneous phenolate solution can be formed, although a homogeneous solution is not to be considered requisite for the success of the reaction. In most cases good results are obtained when the glycol monoalkyl ether and phenolate are used in a 2.5(weight or volume) ratio of about 5:1 to about 20:1, respectively.

The benzyl halide and the phenolate are generally used in equimolecular amounts in accordance with the invention. However, a mole ratio of phenolate to benzyl halide of 4.2:1 to 0.8:1 is also useful. The benzyl halide can be added either in solid form or in pre-dissolved form to the phenolate solution with stirring, the latter at a temperature of 30° to 40° C, for example. This mixture is typically heated to about 110° to 150° C, for example, and kept at this temperature for from about 30 minutes to about 6 hours, depending on the reactivity of the starting components at the given temperature.

It has been found that the process of the invention will produce good volume-time yields when the reaction is performed at temperatures of about 60° to about 180° C, preferably about 80° C to 145° C, at normal pressure. The stated temperature range applies to the temperature of the reaction mixture.

In a preferred embodiment of the invention the mixing is performed at the boiling temperature of the reaction mixture and at normal pressure. Higher temperatures can be employed if super atmospheric pressure is utilized, for example, a pressure up to 40 atmospheres.

In many cases the reaction begins perceptibly at 80° C and usually proceeds very rapidly at temperatures above 110° C. It is desirable to perform the reaction in an apparatus equipped with a reflux condenser and an external heater. The reaction can be performed continuously in a flow-through reactor. In the majority of cases the ethers that form precipitate from the hot mixture while the reaction is still proceeding. In these cases the working up of the products can be accomplished simply by cooling the mixtures and then separating the precipitates by known methods, removing the metal halides by washing with water until the filtrate is halogen-free, and drying the product.

If the ethers that are formed are soluble or to a good extent partially soluble in the reaction mixture, they are isolated by stirring the reaction mixture into water and then proceeding as above.

The new halogenated benzyl ethers can serve as water repellentizing agents for cellulosic textiles.

In order to more fully illustrate the nature of the invention and manner of practicing the same the following examples are presented. Unless otherwise stated, percentages given are percentages by weight. The percentages given in parenthesis after the yields given in grams are weight percentages based upon theory. In these examples the method of the invention is described. It should be understood, however, that the invention is not limited to the specific mode of the examples.

EXAMPLES

EXAMPLE 1

Preparation of 2,3,5,6-tetrachloro-1,4-xylyleneglycol-bis-(pentachlorophenyl)ether:

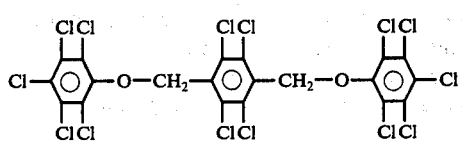

900 g of technical pentachlorophenol sodium (sodium pentachlorophenolate) (approximately 3 moles) was dissolved at 50° C in 6.75 liters of ethylene glycol monomethyl ether and the slightly turbid solution was filtered into a reaction vessel equipped with stirrer and reflux condenser. The pentachlorophenolate solution was heated to about 100° C and, at this temperature, 469.5 g (1.5 moles) of 1,4-bis-(chloromethyl)-2,3,5,6-tetrachlorobenzene were poured into it with stirring.

Thereafter, the mixture was refluxed for 1 hour while the ether that formed began very soon to precipitate. After the mixture had cooled to room temperature, it was suction filtered, and the filter cake was first washed with cold methyl glycol and then, for removal of the sodium chloride content, it was suspended in water, suction filtered again, washed until the filtrate was free of chloride, and the ether was dried.

Yield, 1081 g, corresponding to 93% of the theoretically possible amount.

The raw product melted, after starting to turn brown after 250° C, at 318–319° C with decomposition (black discoloration).

A pure preparation was obtained through recrystallization from a very large amount of boiling chlorobenzene. The melting point was then sharp at 323°–324° C with the formation of a brown melt.

Elemental Analysis: $C_{20}H_4Cl_{14}O_2$ (772.59)
Calculated: C, 31.1%; H, 0.52%; Cl, 64.3%.
Found: C, 31.41% H, 0.47% Cl, 63.95%.

EXAMPLE 2

Preparation of 2,4,5,6-tetrachloro-1,3-xylyleneglycol-bis-(pentachlorophenyl) ether:

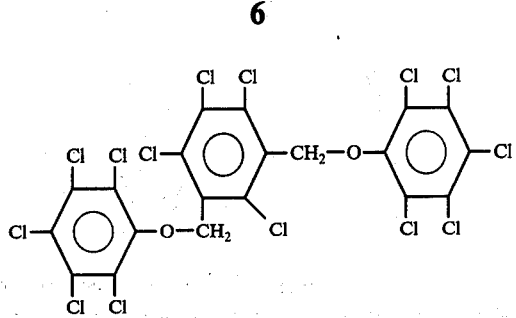

By the procedure described in Example 1, 60 g of technical pentachlorophenol sodium (about 0.2 mole) was dissolved at about 50° C in 450 ml of methyl glycol and the solution was clarified by filtration.

Then, at a temperature between 50° and 60° C, 31.3 g (0.1 mole) of 1,3-bis-(chloromethyl)-2,4,5,6-tetrachlorobenzene was poured into the phenolate solution with stirring, whereupon the benzyl chloride immediately dissolved. The temperature of the reaction mixture was raised to the refluxing temperature (112°–115° C) of the mixture. Even while the temperature was still rising, the reaction began from about 98° C up to 105° C, and the ether that formed precipitated.

To complete the reaction, the mixture was refluxed with stirring for another hour. After it was cooled, the gritty, colorless ether was suction filtered and further processed as in Example 1. 73 grams (94.5%) having a melting point of 294° C after incipient browning at about 245° C were obtained. A small specimen of the substance, recrystallized from a large amount of maleic acid dibutyl ester, melted with black discoloration at 297° C after turning gray at about 280° C.

Elemental Analysis: $C_{20}H_4Cl_{14}O_2$ (772.59)
Calculated: C 31.1% H 0.52%; Cl 64.3%
Found: C 31.19%; H 0.49% Cl 63.99%

EXAMPLE 3

Preparation of p-xylyleneglycol-bis-(pentachlorophenyl) ether:

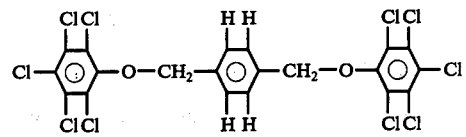

By the procedure described in Example 1 the following were reacted:

900 g of technical pentachlorophenol sodium (3 moles) in 6.75 liters of ethylene glycol monomethyl ether and 200 g (1.5 moles) of α,α'-dichloro-p-xylene.

After filtration and washing as described above, 811 g (85%) of bis-ether was obtained, which melted at 263° C.

One gram of raw ether, recrystallized from 500 ml of methoxyethyl chloride, yielded white, long, matted needles melting at 270° to 272° C.

Elemental Analysis: $C_{20}H_8Cl_{10}O_2$ (634.81)
Calculated: C27.9%; H,1.27% Cl,55.81%.
Found: C,37.68%; H,1.23%; Cl,55.62%.

EXAMPLE 4

Preparation of 4-methyl-2,3,5,6-tetrachlorobenzylalcohol-(1)-(pentachlorophenyl)-ether:

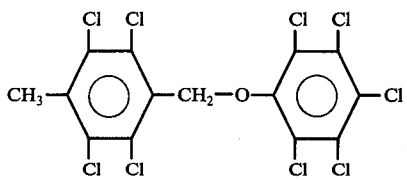

60 g of technical pentachlorophenol sodium (approximately 0.2 mole) was dissolved in 450 ml of methyl glycol at approximately 50° C and the solution was filtered. Then, at 40-50° C, 55.7 g (0.2 mole) of 1-methyl-4-chloromethyl-2,3,5,6-tetrachlorobenzene was poured into the clear phenolate solution with stirring, and the mixture was heated slowly until refluxing began, the complete dissolution of the chloromethyl compound taking place between 60° and 70° C. At slightly above 70° C a reaction started and the ether that formed precipitated. To complete the reaction, stirring was continued for 1 hour at an internal temperature of 110° C.

The product was worked up as described in Example 1. 94 g (92.5%) of raw ether was obtained, in the form of a white powder having a melting point of 254°-256° C. By recrystallization from methoxyethyl chloride at a ratio of 1:300, colorless fine needles were obtained with a melting point of 258°-259° C.

Elemental Analysis: $C_{14}H_5Cl_9O$ (508.27)
Calculated: C 33.15%; H 0.99% Cl 62.86%
Found: C 32.9% H 1.01% Cl 62.62%

EXAMPLE 5

Preparation of pentachlorobenzylalcohol-(pentachlorophenyl)-ether:

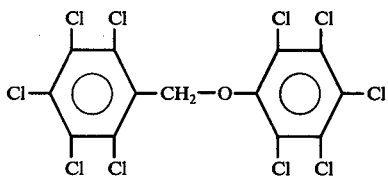

This ether was prepared by reacting, by the procedure of Example 1, 60 g (about 0.2 mole) of pentachlorophenol sodium, 400 ml of methyl glycol and 60 g (about 0.2 mole) of pentachlorobenzyl chloride. In this case, the ether precipitated between 45° and 60° C. After the reaction mixture has cooled, the product that had separated in a sago-like form was removed by suction filtering and worked up as described above. 88 g (83%) having a melting point of 264° to 266° C was obtained.

If one gram of the crude ether is recrystallized from 60 ml of 1,2-dibromoethane, an analytically pure preparation is obtained having a melting point of 265°-267° C.

Elemental Analysis: $C_{13}H_2Cl_{10}O$ (528.68)
Calculated: C 29.60%; H 0.38%; Cl 67.12%
Found: C 29.48%; H 0.33%; Cl 60.93%

EXAMPLE 6

Preparation of p-xylyleneglycol-bis-(2,4,6-tribromophenyl)-ether:

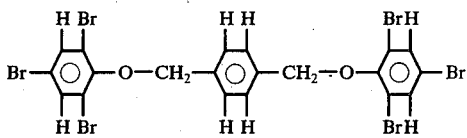

66.2 g (0.2 mole) of 2,4 6-tribromophenol in 450 ml of methyl glycol was placed at room temperature in a reaction vessel equipped with stirrer and reflux condenser, and a solution of 11.2 g (0.2 mole) of potassium hydroxide in 15 ml of water was added. The temperature of the mixture rose to 35° C.

Then 17.5 g (0.1 mole) of α,α'-dichloro-p-xylene was put into the resultant phenolate solution and the temperature was raised rapidly to 130° C bath temperature. At an internal temperature of about 66° C, the reaction definitely commenced and the ether that formed began to precipitate as a white powder. Refluxing was continued for one more hour, with stirring. After the reaction mixture cooled, the ether was removed by suction filtering, washed with water and dried.

65.8 (86%) of the ether was obtained, having a melting point of 222°-225° C. After recrystallization from a very large amount of methoxyethyl chloride, long needles were obtained having a melting point of 230°-232° C.

Elemental Analysis: $C_{20}H_{12}Br_6O_2$ (763.77)
Calculated: C 31.47% H 1.58%; Br 62.7%
Found: C 31.38%; H 1.45%; Br 62.61%

EXAMPLE 7

Preparation of 2,3,5,6-tetrachloro-p-xyleneglycol-bis-(2,4,6-tribromophenyl) ether:

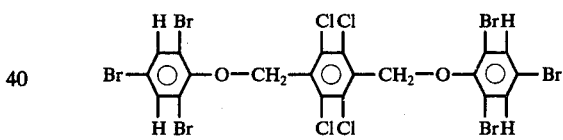

In the same apparatus as in Example 1, 66.2 g (0.2 mole) of 2,4,6-tribromophenol was dissolved in 900 ml of ethylene glycol monoethyl ether (ethyl cellosolve) with the addition of a solution of 8 g (0.2 mole) of sodium hydroxide in 8 ml of water.

31.3 g (0.1 mole) of 1,4-bis-(chloromethyl)-2,3,5,6-tetrachlorobenzene was stirred into this phenolate solution between 30° and 40° C, and the mixture was heated for 45 minutes, with stirring, to an internal temperature of 115° C. At around 100° C the bis-ether began to precipitate from the reaction mixture as a colorless powder. The powder was processed as described above and 78.5 g (87%) of bis ether was obtained with a decomposition point of 274°-277° C after turning brown beginning at 245° C.

By recrystallization from a large amount of nitrobenzene, the substance was obtained in colorless needles which start to discolor at 280° C, becoming increasingly darker as the temperature increased. It did not melt until about 360° C.

Elemental Analysis: $C_{20}H_8Br_6Cl_4O_2$.
Calculated: C,26.65%; H,0.89%; Br, 53.2%; Cl,15.73%.
Found: C,26.48%; H,0.84%; Br,52.94%; Cl,15.82%,

EXAMPLE 8

Preparation of 2,4,5,6-tetrachloro-m-xylyleneglycol-bis-(2,4,6-tribromophenyl) ether:

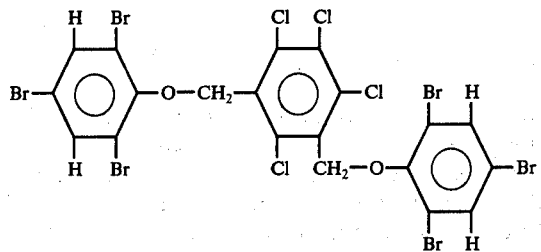

66.2 g (0.2 mole) of 2,4,6-tribromophenol was suspended at room temperature in 450 ml of methyl glycol and was made into a phenolate solution by mixing with a solution of 8 g (0.2 mole) of sodium hydroxide in 8 ml of water.

31.3 g (0.1 mole) of 1,3-bis-(chloromethyl)-2,4,5,6-tetrachlorobenzene was stirred into this solution at 30°–40° C and the mixture was heated to the refluxing temperature. At this temperature it was allowed to react for 1 hour with stirring. The bis-ether precipitated in the form of small, colorless needles, which were separated as described before. When they were recrystallized from a large amount of nitrobenzene, a microcrystalline powder was obtained with a melting point of 266°–268° C (decomposition).

Elemental Analysis: $C_{20}H_8Br_6Cl_4O_2$ (901.55)
Calculated: C, 26.65%; H, 0.89%; Br, 53.2% Cl, 15.73%.
Found: C, 26.53%; H, 0.82%; Br 53.38%; Cl 15.51%.

EXAMPLE 9

Preparation of 4-methyl-2,3,5,6-tetrachlorobenzylalcohol-(2,4,6-tribromophenyl)-ether:

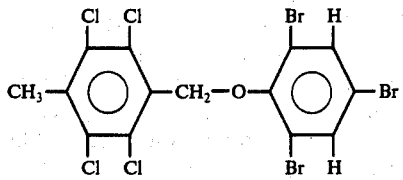

As in the preceding example, 66.2 g (0.2 mole) of 2,4,6,-tribromophenol, 8 g (0.2 mole) of sodium hydroxide in 8 ml of water, 900 ml of methylglycol and 55.7 g (0.2 mole) of 1-chloromethyl-4-methyl-2,3,5,6-tetrachlorobenzene were reacted for 1 hour at 115° C. The reaction started at 80° C. The product was separated and washed in the manner previously described. 106 g (92.3%) of the desired ether was obtained as a white powder melting at 208°–211° C, which after recrystallization from a large amount of methoxyethyl chloride melted at 211°–212° C.

Elemental Analysis: $C_{14}H_7Br_3Cl_4O$ (572.75)
Calculated: C, 29.35%; H, 1.23%; Br, 41.8%; Cl, 24.7%.
Found: C 29.18%; H, 1.11%; Br, 41.7%; Cl 25.03%.

EXAMPLE 10

Preparation of 4-methylbenzylalcohol-(2,4,6-tribromophenyl) ether:

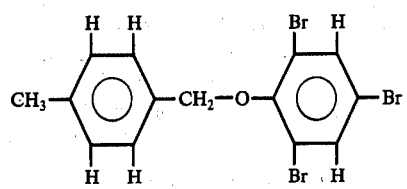

In the manner described in the foregoing examples, 450 ml of methyl glycol, 66.2 g (0.2 mole) of 2,4,6-tribromophenyl, 8 g (0.2 mole) of sodium hydroxide in 8 ml of water, and 28.15 g (0.2 mole) of 1-chloromethyl-4-methyl-benzene were reacted. The reaction began perceptibly at 80° C. This ether precipitated in only small quantity during the reaction, most of it crystallizing in the form of needles when the reacted mixture cooled. After suction filtering, washing and drying, 71 g (81.5%) was obtained having a melting point of 98°–100° C. The pure ether, with a melting point of 100°–102° C, was obtained by recrystallization from methyl glycol.

Elemental Analysis: $C_{14}H_{11}Br_3O$ (434.97)
Calculated: C 38.7%; H 2.55%; Br 55.2%
Found: C 38.56%; H 2.37%; Br 55.39%

EXAMPLE 11

Preparation of pentabromophenylbenzyl ether:

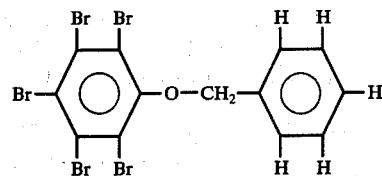

750 ml of methyl glycol, 97.75 g (0.2 mole) of pentabromophenol, 8 g (0.2 mole) of sodium hydroxide in 8 ml. of water, and 25.32 g (0.2 mole) of benzyl chloride were reacted as described in the preceding examples. The reaction started around 75° C and the ether precipitated in the form of fibrous needles. Yield 91 g (79%) melting at 200°–201° C. When 10 g of the product was recrystallized from 200 ml of methoxyethyl chloride, the melting point increased to 202°–203° C.

Elemental Analysis: $C_{13}H_7Br_5O$ (578.75)
Calculated: C 27.45%; H 1.22%; Br 69.0%
Found: C 27.19%; H 1.12% Br 68.95%

EXAMPLE 12

Preparation of pentabromophenyl-(4-methylbenzyl) ether:

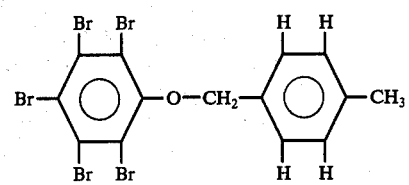

600 ml. of methyl glycol, 97.75 g (0.2 mole) of pentabromophenol, 8 g (0.2 mole) of sodium hydroxide in 8 ml of water, and 28.12 g (0.2 mole) of 1-chloromethyl-4-methyl-benzene were reacted in the manner previously described. At 65° C the reaction perceptibly commenced. The ether crystallized in long needles during the refluxing of the mixture. Yield: 96 g (81%), M.P. 194° C. 10 g recrystallized from 300 ml of methoxyethyl chloride had a melting point of 200°-202° C.

Elemental Analysis: $C_{14}H_9Br_5O$ (592.77)
Calculated: C 28.4%; H 1.53%; Br 67.4%
Found: C 28.50%; H 1.38% Br 67.20%

EXAMPLE 13

Preparation of p-xyleneglycol-bis(pentabromophenyl) ether:

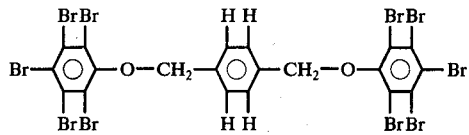

600 ml of ethyl cellosolve, 97.75 g (0.2 mole) of pentabromophenol, 8 1 g (0.2 mole) of sodium hydroxide in 8 ml of water, and 17.5 g (0.1 mole) of α,α'-dichloro-p-xylene were combined by the procedure previously described and reacted for 90 minutes at 120° C, with stirring. Beginning at an internal temperature of 80° C, the bis-ether precipitated from the reaction solution as a fine powder. Filtration, washing and drying are performed as in the previous examples. 95.2 g (88%) of raw product was obtained which had a decomposition point at 253° C after turning gray beginning at 202° C. This ether crystallized out of a large amount of nitrobenzene in the form of colorless needles which turn light brown at 298° C, and medium brown up to 360° C, and up to 360° C do not melt.

Elemental Analysis: $C_{20}H_8Br_{10}O_2$ (1,079.37)
Calculated: C,22.25%; H,0.75%; Br, 74.02%.
Found: C,22.41%; H,0.62%; Br, 73.95%.

EXAMPLE 14

Preparation of (4-methyl-2,3,5,6-tetrachlorobenzyl)-pentabromophenyl ether:

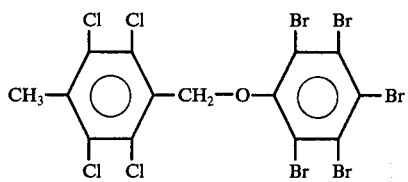

1000 ml of methyl glycol, 97.75 g (0.2 mole) of pentabromophenol, 8 g (0.2 mole) of sodium hydroxide in 8 ml of water, and 55.7 g (0.2 mole) of 4-methyl-1-chloromethyl-2,3,5,6-tetrachlorobenzene are combined as described above and reacted at 110° C for 1 hour, with stirring, and then worked up as specified. 128.5 g (87.5%) of raw ether was obtained which melted at 254°-255° C with brown discoloration. Upon recrystallization from nitrobenzene, colorless, matted small needles were obtained which melted at 266°-268° C (brown melt).

Elemental Analysis: $C_{14}H_5Cl_4O$ (730.55)
Calculated: C 23.0%; H 0.69%; Br 54.6%; Cl 19.4%
Found: C 23.21%; H 0.62%; Br 54.4%; Cl 19.68%

EXAMPLE 15

Preparation of (2-methyl-3,4,5,6-tetrachlorobenzyl)-pentabromophenyl ether:

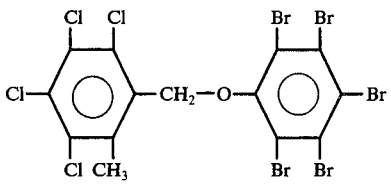

In the manner described in Example 1, 450 ml of methyl glycol, 24.5 g (0.05 mole) of pentabromophenol, 2 g (0.05 mole) of sodium hydroxide in 4 ml of water, and 13.95 g (0.05 mole) of 1-chloromethyl-2-methyl-3,4,5,6-tetrachlorobenzene were reacted for 1 hour at the refluxing temperature. Even at 75° C the ether began to precipitate in microcrystalline form. After the usual processing, 32.6 g (87%) of a finely crystalline, colorless powder melting at 288°-291° C was obtained. One gram recrystallized from 60 ml of xylene had a melting point of 291°-293° C. Repeated recrystallization from xylene produced no further change in the melting point.

Elemental Analysis: $C_{14}H_5Br_5Cl_4O$ (730.55)
Calculated: C 23.0% H 0.69% Br 54.6% Cl 19.4%
Found: C 22.87% H 0.63%; Br 54.97% Cl 19.14%

EXAMPLE 16

Preparation of 1,4-(2,3,5,6-tetrachloroxylyleneglycol)-bis-pentabromophenyl ether:

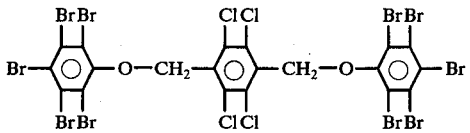

a. From 1,4-bis-(chloromethyl)-2,3,5,6-tetrachlorobenzene:

3 liters of ethyleneglycol monobutyl ether, 195.5 g (0.4 mole) of pentabromophenol, 16g (0.4 mole) of sodium hydroxide in 20 ml of water, and 62.6 (0.2 mole) of 1,4-bis-(chloromethyl)-2,3,5,6-tetrachlorobenzene were reacted together by the method of the invention for 1 hour at 120° C, the reaction starting perceptible at 80°-85° C. Even at this temperature the bisether started to precipitate. By the usual processing 192 g was obtained (79%) of raw ether in the form of a nearly colorless powder melting at 263°-264° C, which when recrystallized by nitrobenzene gave colorless needles having a melting point of 277°-280° C (decomposition).

Elemental Analysis: $C_{20}H_4Br_{10}Cl_4O_2$ (1,217.15)
Calculated: C,19.75%; H 0.33%; Br, 65.70% Cl,11,65%.
Found: C,19.94%; H,0.26%; Br,65.42%; Cl 11.78%.

b. From 1,4-bis-(bromomethyl)-2,3,5,6-tetrachlorobenzene:

The procedure was the same as in a) except that 80.5 g (0.2 mole) of α,α'-dibromotetrachloro-p-xylene was used as the benzyl halide and the process was performed in 3 liters of methyl glycol. Yield 196 g (81%), M.P. 261°-263° C.

EXAMPLE 17

Preparation of 1,3-(2,4,5,6-tetrachloroxylyleneglycol)-bis-pentabromophenyl ether:

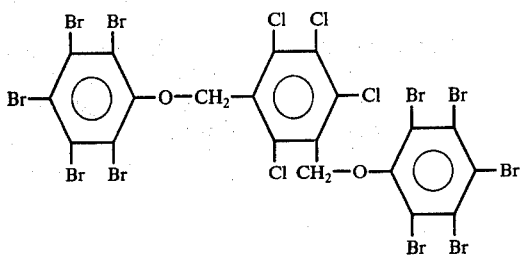

Similarly to Example 1, 1.1 liter of methyl glycol, 97.75 g (0.2 mole) of pentabromophenol, 8 g (0.2 mole) of sodium hydroxide in 8 ml of water, and 31.3 g (0.1 mole) of 1,3-bis-(chloromethyl)-2,4,5,6-tetrachlorobenzene were reacted at 110° C for 1 hour. After processing in the previously descrbed manner, 107 g (88%) was obtained of the bis-ether in the form of a colorless powder having a melting point of 254°–255° C with decomposition. When crystallized from a large amount of xylene the substance had a melting point of 259°–261° C (decomposition).

Elemental analysis: $C_{20}H_4Br_OCl_4O_2$ (1,217.15)

Calculated: C 19.75%; H 0.33%; Br 65.70%; Cl 11.65%

Found: C 19.91%; H 0.22%; Br 65.59%; Cl 11.82%

EXAMPLE 18

Into a solution of about 10%, by weight, of the ether of Example 10, at a temperature of 50° C, a wad of viscose fibers was immersed and then dried by evaporation of the solvent. The water absorption capacity of the fiber wad thus hydrophobized was approximately 22% smaller than in the original fibers.

What is claimed is:

1. A process for preparing a benzyl ether of the formula:

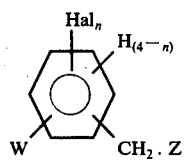

I wherein W is a chlorine or bromine atom, a methyl radical or a radical —CH$_2$. Z and is disposed in the ortho, meta or para bromine, n is 0 to 4 and Z is a phenoxy radical of the general formula:

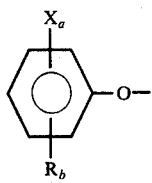

II wherein X is chlorine or bromine, R is hydrogen, an alkyl radical of 1 to 4 carbon atoms, a is 2 to 5 and b is (5-a) which consists essentially of contacting a benzyl halide of the formula:

III

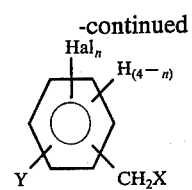

wherein Hal, n, X have the previously assigned significance, Y is CH$_2$X or a methyl radical, said Y being disposed in the ortho, meta or para position with respect to the radical —CH$_2$X, at an elevated temperature in the presence of a reaction medium of a monoalkyl ether of glycols selected from the group consisting of 1,4-butanediol, 2,3-butylene glycol, propylene glycol or ethylene glycol where the alkyl group has 1 to 4 carbon atoms, an alkali or alkaline earth metal phenolate of a halogen phenol having the formula:

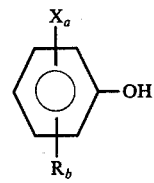

IV wherein X, R, a and b have the previously assigned significance and thereafter separating the resultant aromatic polynuclear halogenated benzyl ether.

2. A process according to claim 1 wherein the glycol monoalkyl ether is ethylene glycol monomethyl ether or ethylene glycol monoethyl ether.

3. A process according to claim 1 wherein the reaction is conducted at the boiling temperature of the reaction mixture.

4. A process according to claim 1 wherein the phenolate is an alkali metal phenolate.

5. A process according to claim 4 wherein the alkali metal is sodium or potassium.

6. A process according to claim 4 wherein the phenolate is prepared in situ by the reaction of a halogen phenol of the above formula with an aqeuous solution of an alkali metal hydroxide in the glycol monoalkyl ether reaction medium.

7. A process according to claim 1 wherein the benzyl halide is selected from the group consisting of pentachlorobenzylchloride, 1-methyl-2-chloromethyl-3,4,5,6-tetrachlorobenzene, 1-methyl-3-chloromethyl-2,4,5,6-tetrachlorobenzene, 1-methyl-4-chloromethyl-2,3,5,6-tetrachlorobenzene, the isomeric o-, m- and p-methylbromomethyltetrachlorobenzenes, 1,2-bis-(chloromethyl)-3,4,5,6-tetrachlorobenzene, 1,2-bis-(bromomethyl)-3,4,5,6-tetrachlorobenzene, ,3-bis (chloromethyl)-2,4,5,6-tetrachlorobenzene, 1,3-bis-(bromomethyl)-2,4,5,6-tetrachlorobenzene, 1,4-bis-(chloro- or bromomethyl)-2,3,5,6-tetrachlorbenzne and α,α'-dichloro(bromo)-p-xylene.

8. A process according to claim 1 wherein the phenolate is an alkali or alkaline earth metal phenolate of a halogen phenol selected from the group consisting of pentabromophenol, pentachlorophenol, 2,4-dichloro-6-methylphenol, 2,5-dichloro-6-methylphenol, 2,4,6-trichlorophenol, 2,4,6-tribromophenol, 2,3,4,6-tetrachlorophenol, 2,4,6-trichloro-3,5-dimethylphenol, 2,4-dichloro-3-methyl-6-tert.-butylphenol and 4,5-dichloro-2,6-di-tert.-butylphenol.

9. A process according to claim 1 wherein the reaction of the benzyl halide with the phenolat is carried out at a temperature between 60° and 180° C.

10. A process according to claim 9 wherein the reaction is conducted at atmospheric pressure.

11. A process according to claim 10 wherein the reaction is conducted at a temperature between 65° and 145° C.

12. A process according to claim 1 wherein a reaction mixture consisting essentially of said benzyl halide, said phenolate and said glycol monoalkyl ether is formed and said benzyl halide is reacted with said phenolate at a temperature of between 60° and 180° C.

* * * * *

UNITED STATES PATENT AND TRADEMARK OFFICE
CERTIFICATE OF CORRECTION

PATENT NO. : 4,039,587
DATED : August 2, 1977
INVENTOR(S) : Egon Norbert Petersen It is certified that error appears in the above-identified patent and that said Letters Patent are hereby corrected as shown below:

Abstract, 2nd column, line 3, below first formula, "(5-ia)" should be --(5-a)--.

Column 6, line 63, "27.9%" should be -- 37.9% --.

Column 7, line 64, "60,93%" should be -- 66.93% --.

Column 9, line 29, after "before." insert -- 79g (87.5%), having a melting point 253-254°C. --.

Column 11, line 20, "81g" should be -- 8 g --.

Column 11, line 62, insert -- $Br_5$ -- after "$C_{14}H_5$" in formula.

Column 12, line 47, "bisether" should be -- bis-ether --.

Column 13, line 18, "descrbed" should be -- described --.

Column 13, line 24, "$Br_0$" should be -- $Br_{10}$ --.

Column 13, line 51, insert -- position with respect to $CH_2.Z$, and Hal is a chlorine or -- after "para".

Signed and Sealed this

Twenty-eighth Day of March 1978

[SEAL]

Attest:

RUTH C. MASON
Attesting Officer

LUTRELLE F. PARKER
Acting Commissioner of Patents and Trademarks